(12) United States Patent
Prat-Lacondemine

(10) Patent No.: US 8,410,267 B2
(45) Date of Patent: Apr. 2, 2013

(54) REGIOSELECTIVE REDUCTION OF FUSED PYRROLOCARBAZOLES-5,7-DIONES

(75) Inventor: Laurence Prat-Lacondemine, Pontault Combault (FR)

(73) Assignee: Teva Sante, La Defense Cedex (Paris) (FR)

( * ) Notice: Subject to any disclaimer, the term of this patent is extended or adjusted under 35 U.S.C. 154(b) by 70 days.

(21) Appl. No.: 13/105,455

(22) Filed: May 11, 2011

(65) Prior Publication Data
US 2011/0224436 A1  Sep. 15, 2011

Related U.S. Application Data

(63) Continuation of application No. PCT/EP2009/065930, filed on Nov. 26, 2009.

(30) Foreign Application Priority Data

Nov. 27, 2008 (EP) ..................................... 08305856

(51) Int. Cl.
*C07D 487/14* (2006.01)
(52) U.S. Cl. ..................................... 544/331; 548/358.1
(58) Field of Classification Search ........................ None
See application file for complete search history.

*Primary Examiner* — Sun Jae Loewe

(57) ABSTRACT

The present invention relates to a method for regioselectively reducing the maleimide compounds of formula (I). The invention also relates to $C_7$ hydroxy lactam regioisomers of formula (II) obtainable by this method and their use for the preparation of lactams of formula (III) which are particularly useful as intermediate for the synthesis of fused pyrrolocarbazoles.

12 Claims, No Drawings

REGIOSELECTIVE REDUCTION OF FUSED PYRROLOCARBAZOLES-5,7-DIONES

CROSS REFERENCE TO RELATED APPLICATIONS

This application is a continuation application of International Application No. PCT/EP2009/065930, filed Nov. 26, 2009, which claims priority to European Application Number EP08305856.0, filed Nov. 27, 2008. The disclosures of the aforementioned applications are incorporated herein by reference in their entireties for all purposes.

FIELD OF THE INVENTION

The present invention relates to a method for regioselectively reducing the maleimide compounds of formula (I). The invention also relates to $C_7$ hydroxy lactam regioisomers of formula (II) obtainable by this method and their use for the preparation of lactams of formula (III) which are particularly useful as intermediate for the synthesis of fused pyrrolocarbazoles.

BACKGROUND OF THE INVENTION

Various synthetic small organic molecules that are biologically active and generally known in the art as "fused pyrrolocarbazoles" have been prepared (see U.S. Pat. Nos. 5,475,110; 5,591,855; 5,594,009; 5,616,724; and 6,630,500). In addition, U.S. Pat. No. 5,705,511 discloses fused pyrrolocarbazole compounds which possess a variety of functional pharmacological activities. The fused pyrrolocarbazoles were disclosed to be used in a variety of ways, including: enhancing the function and/or survival of cells of neuronal lineage, either singularly or in combination with neurotrophic factor(s) and/or indolocarbazoles; enhancing trophic factor-induced activity; inhibition of protein kinase C ("PKC") activity; inhibition of trk tyrosine kinase activity; inhibition of proliferation of a prostate cancer cell-line; inhibition of the cellular pathways involved in the inflammation process; and enhancement of the survival of neuronal cells at risk of dying.

Fused pyrrolocarbazole compounds of formula (I) and notably of formula (III) are disclosed in U.S. Pat. No. 7,169,802 (Scheme 1). In particular, among compounds of formula (III), there is disclosed the compound of the following formula:

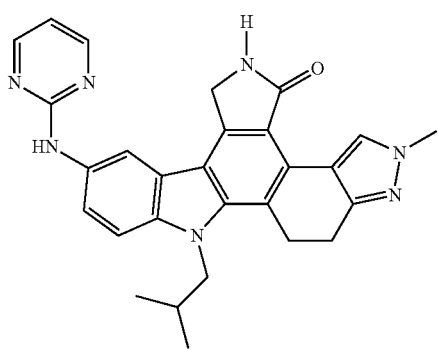 [SMILES: CC(C)Cn1c2ccc(Nc3ncccn3)cc2c2c3c(c4c(c21)CCc1nn(C)cc1-4)C(=O)NC3]

This compound, also known as 11-Isobutyl-2-methyl-8-(2-pyrimidinylamino)-2,5,6,11,12,13-hexahydro-4Hindazolo[5,4-a]pyrrolo[3,4-c]carbazol-4-one is a potent, orally-active TIE-2/VEGF-R inhibitor having anti-tumor and anti-angiogenic activity.

These compounds are prepared from fused pyrrolocarbazoles 5-oxo lactam regioisomers as intermediates (see notably 1-34) which are prepared by a Diels Alder reaction followed by a reduction of the CN group and an intramolecular condensation of the resulting amine function with the ester function into a lactam (Scheme 2).

Scheme 1

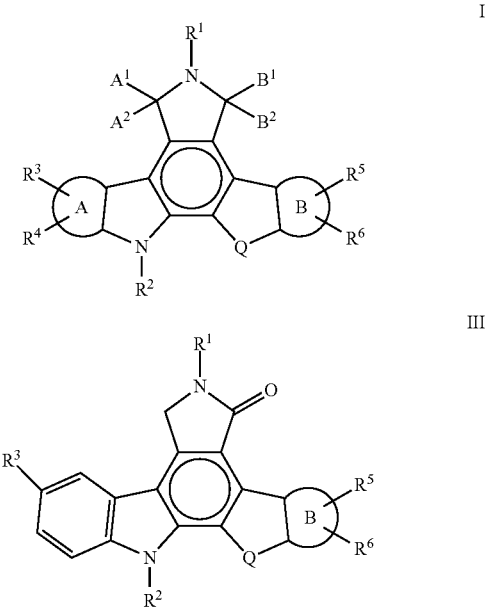

Scheme 2

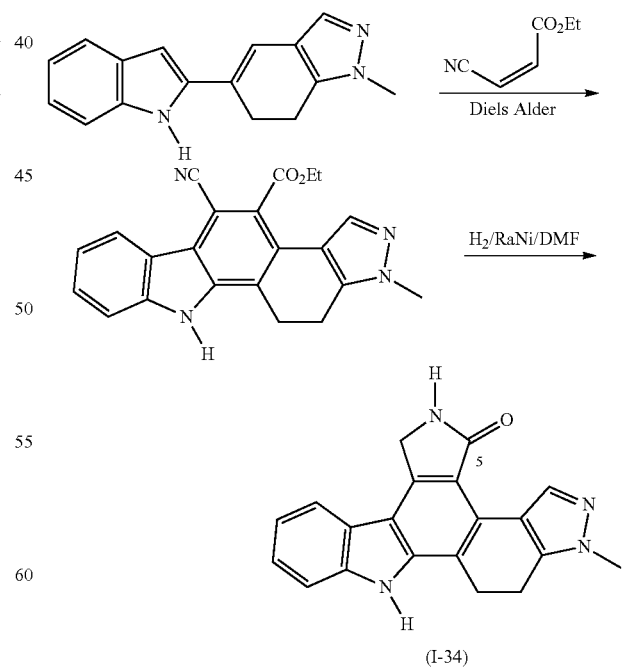

However, the Diels Alder reaction involved in this synthetic method displays a low regioselectivity. Further, an hydrogenation under pressure is required. Thus, this synthetic pathway cannot be easily scaled up to commercial implementation.

Another approach for preparing such 5-oxo lactam regioisomers consists in selectively reducing the corresponding maleimides.

Such an approach has been disclosed in R. L. Hudkins et al., J. Heterocyclic Chem., 38, 591 (2001) which relates to the synthesis of heteroaryl fused pyrrolo[3,4-c]carbazoles and more particularly to benzo[b]thieno- and benzo[b]furano[2,3-a]pyrrolo[3,4-c]carbazole (Scheme 3). In this method, the maleimide is reduced to the 5-oxo and 7-oxo lactam regioisomers using a Clemmensen reduction (zinc.mercury almalgam, ethanol, hydrochloric acid). The lactam isomers are formed in approximately 60-65% as a mixture of 7-oxo: 5-oxo isomers in a ratio of 2:1 for a7: a5 and 3:1 for b7:b5.

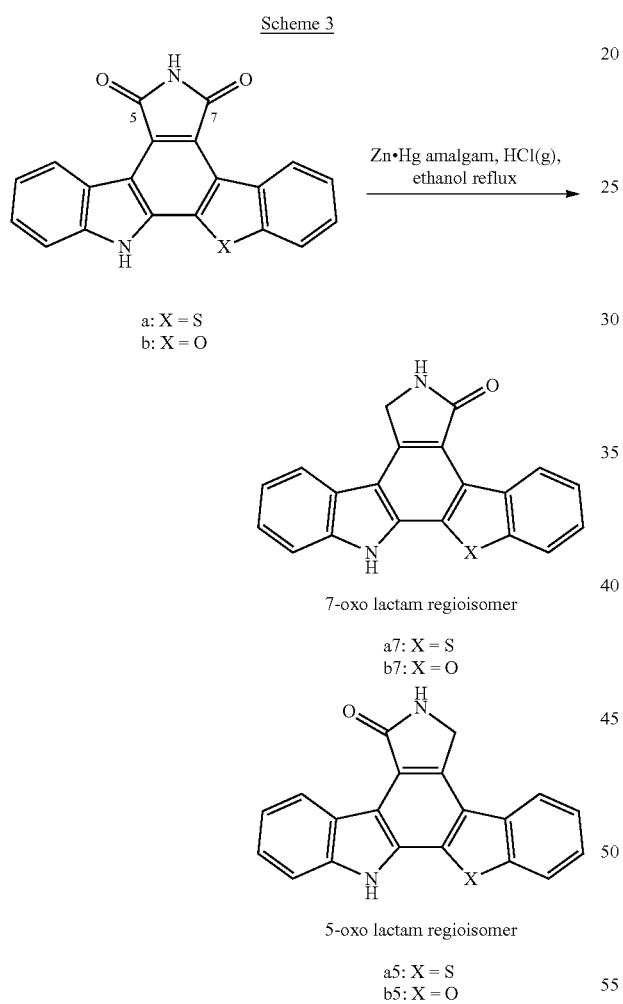

This method has also been applied to the synthesis of indeno[2,1-a]pyrrolo[3,4-c]carbazole lactam regioisomers (R. L. Hudkins et al., J. Heterocyclic. Chem., 40, 135 (2003)) (Scheme 4). The lactam regioisomers are obtained by subjecting the maleimide to a Clemmensen reduction (Zn.Hg amalgam, HCl(g), ethanol reflux). In these conditions, a 4:1 mixture of the 5-oxo and 7-oxo lactam isomers is obtained with a yield of 50%.

Hence moderate regioselectivities and yields are reported using a Clemmensen reduction for preparing pyrrolocarbazoles 5-oxo and/or 7-oxo lactam regioisomers. In this respect, it should be noted that these results are based on the ratio of regioisomers recovered after purification on a column chromatography and may not reflect the actual regioselectivity of the reaction. Further, heavy metals such as Zn or Hg are acceptable only in very low amounts in the pharmaceutical products and cumbersome subsequent purification steps are thus needed to eliminate traces of such metals.

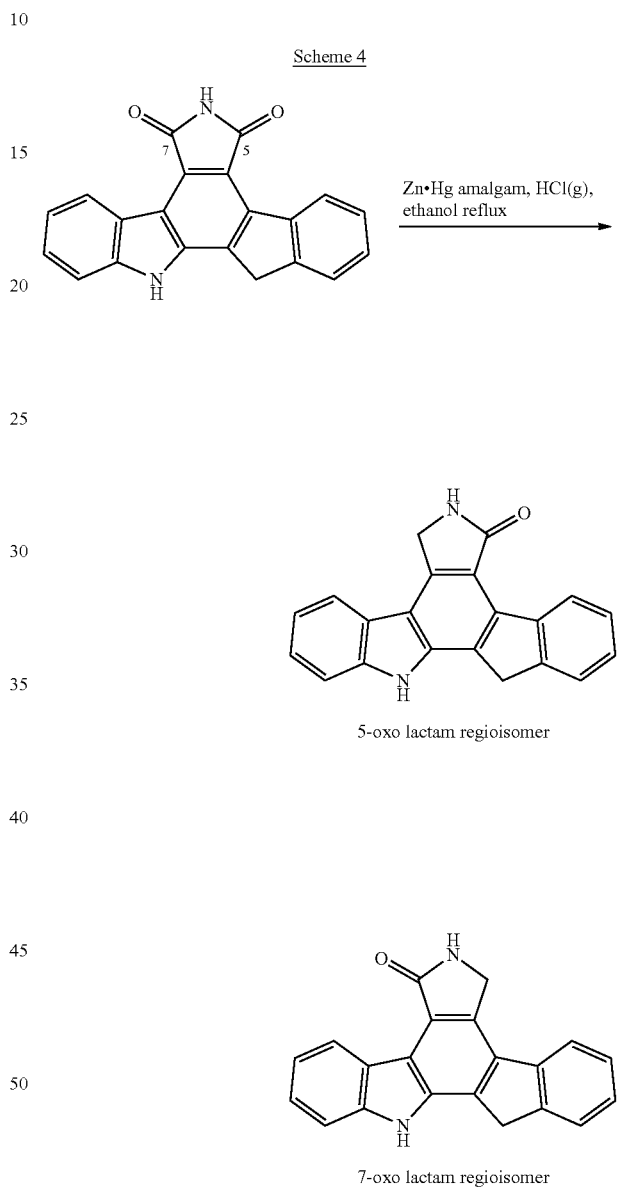

The issue of regioselectivity in the formation of a lactam from a nearly symmetric imide precursor has also been addressed in the context of the synthesis of staurosporine which structure also includes a fused pyrrolocarbazole heterocycle (J. T. Link et al., J. Am. Chem. Soc. 1995, 117, 552-553) (Scheme 5). In this process, the imide precursor is reduced with sodium borohydride and the obtained carbanolamide is then deoxygenated via the action of benzeneselenol. However, this two step sequence is not regioselective and leads to a 1:1 mixture of isostausporine and staurosporine with low yields.

Scheme 5

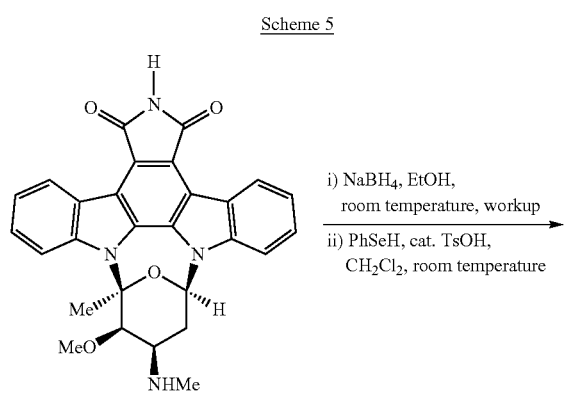

i) NaBH₄, EtOH,
room temperature, workup ii) PhSeH, cat. TsOH,
CH₂Cl₂, room temperature

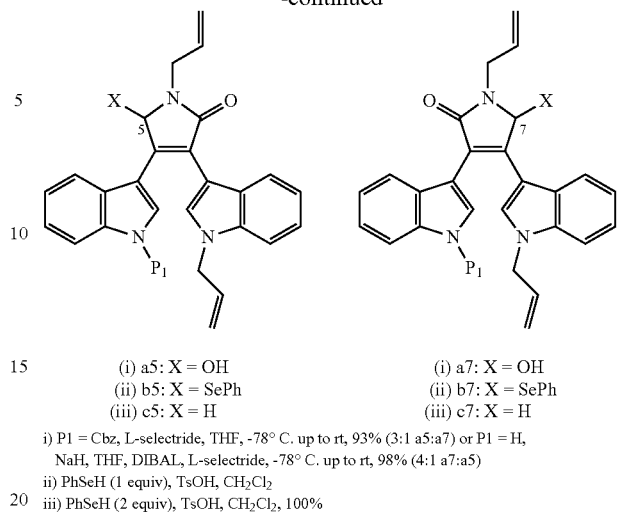

(i) a5: X = OH
(ii) b5: X = SePh
(iii) c5: X = H (i) a7: X = OH
(ii) b7: X = SePh
(iii) c7: X = H i) P1 = Cbz, L-selectride, THF, -78° C. up to rt, 93% (3:1 a5:a7) or P1 = H, NaH, THF, DIBAL, L-selectride, -78° C. up to rt, 98% (4:1 a7:a5)
ii) PhSeH (1 equiv), TsOH, CH₂Cl₂
iii) PhSeH (2 equiv), TsOH, CH₂Cl₂, 100%

However, this method which requires very low temperature conditions and an expensive chiral reducing agent, cannot be easily scaled up to commercial implementation.

Therefore, there is a need for an improved regioselective process for the manufacture of 5-oxo lactam regioisomers as intermediates of structurally related fused pyrrolocarbazoles which overcomes the drawbacks of the prior art and, in particular, allows to obtain satisfactory yields.

SUMMARY OF THE INVENTION

The present invention in one aspect provides a novel process for regioselective reduction of maleimides of formula (I) into the hydroxy lactams of formula (II), which process allows obtaining the corresponding 5-oxo lactam regioisomer of formula (III) with surprisingly high regioselectivities along with satisfactory yields:

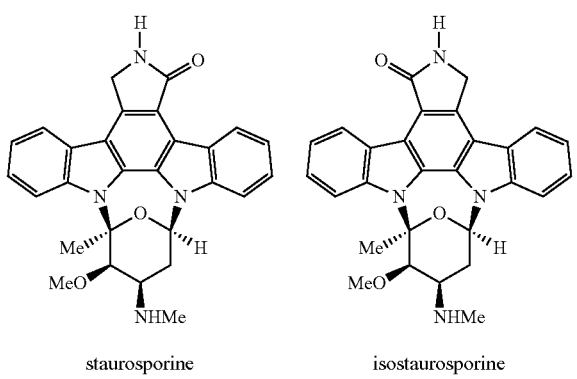

staurosporine    isostaurosporine

Another method for the regioselective reduction of maleimide in the course of staurosporine synthesis has also been disclosed in J. T. Link et al., J. Am. Chem. Soc. 1996, 118, 2828-2842 (Scheme 6).

Scheme 6

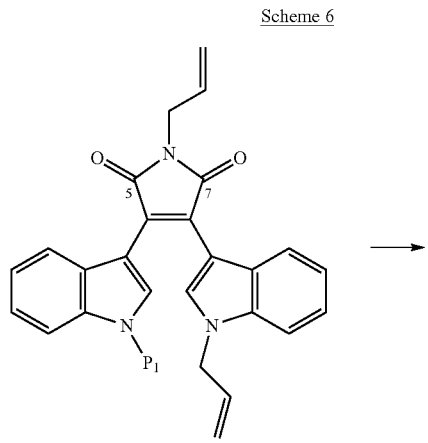

Scheme 7

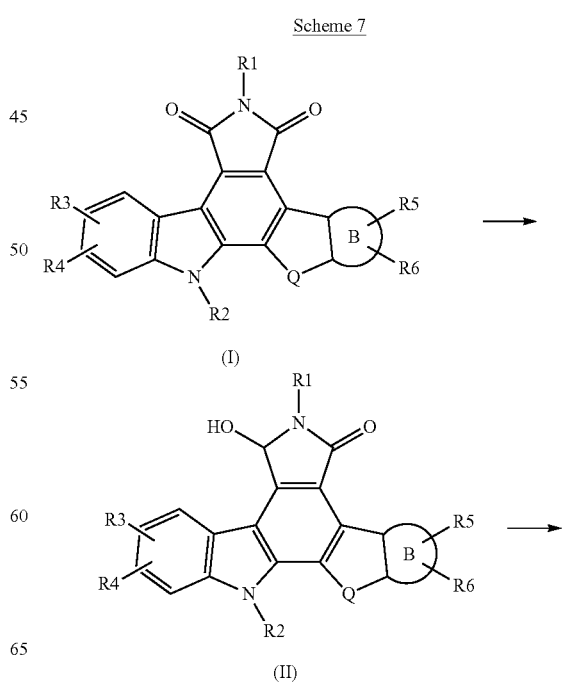

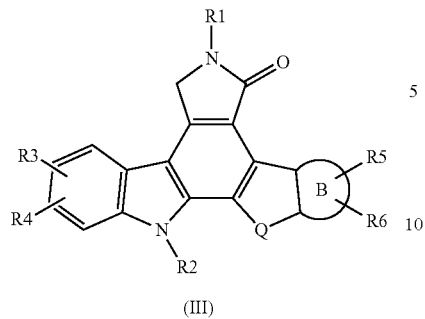

(III)

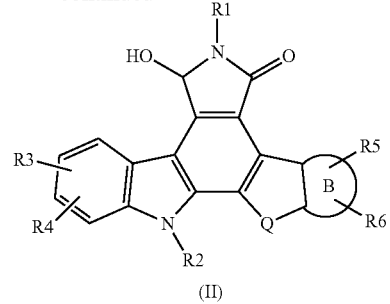

(II)

wherein the constituent members are defined infra.

More specifically, it has been discovered that the reduction of the maleimide of formula (I) in the presence of a metal hydride and an activating agent leads regioselectively to the formation of the $C_7$ hydroxy lactam ($C_7$ position according to the above numbering). Now, as a further advantage, this latter can be easily and selectively further reduced into the corresponding lactam, thus leading to 5-oxo lactam regioisomers of formula (III) with surprisingly high regioselectivities that could reach more than 95% and notably of about 98% referring to maleimides of formula (I).

Another object of the present invention is to provide novel compounds of formula (II), which compounds are useful intermediates for the regioselective reduction of maleimides of formula (I) into 5-oxo lactam regioisomers of formula (III).

Another object of the present invention is to provide a method for reducing said compounds of formula (II) into said compounds of formula (III).

A further object of the present invention is to provide a use of the compounds of formula (II) for the preparation of the fused pyrrolocarbazole compounds disclosed in U.S. Pat. No. 7,169,802 and U.S. patent application No. 2006/0247294.

These and other objects, features and advantages of compounds of formula (A) will be disclosed in the following detailed description of the patent disclosure.

DETAILED DESCRIPTION

Thus, in one aspect, the invention provides a method for regioselectively reducing a compound of formula (I) into a compound of formula (II):

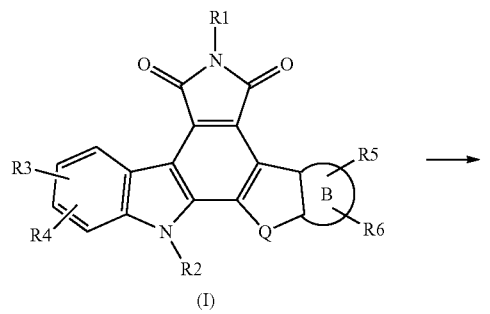

(I)

wherein:
ring B, together with the carbon atom to which it is attached, is selected from:
(a) a phenylene ring in which from 1 to 3 carbon atoms may be replaced by nitrogen atoms; and
(b) a 5-membered aromatic ring in which either
(1) one carbon atom may be replaced with an oxygen, nitrogen, or sulfur atom;
(2) two carbon atoms may be replaced with a sulfur and a nitrogen atom, an oxygen and a nitrogen atom, or two nitrogen atoms; or
(3) three carbon atoms may be replaced with three nitrogen atoms, one oxygen and two nitrogen atoms, or one sulfur and two nitrogen atoms;

$R^1$ and $R^2$ are each independently selected from H, optionally substituted alkyl, optionally substituted alkenyl, optionally substituted alkynyl, optionally substituted cycloalkyl, and optionally substituted heterocycloalkyl, wherein said optional substituents are one to three $R^{10}$ groups;

at least one of $R^3$, $R^4$, $R^5$, and $R^6$ is selected from H, (alkylene)$_x$OR$^{13}$, (CH$_2$)$_p$OR$^{22}$, O-(alkylene)-R$^{27}$, OCH[(CH$_2$)$_p$OR$^{20}$]$_2$, NR$^{11}$R$^{32}$, NR$^{11}$R$^{33}$, (alkylene)-NR$^{18}$R$^{19}$, substituted alkyl, wherein one of the substituents is a spirocycloalkyl group, optionally substituted (alkylene)$_x$-cycloalkyl, and optionally substituted -(alkylene)$_x$-heterocycloalkyl, wherein the heterocycloalkyl does not include unsubstituted N-morpholinyl, N-piperidyl, or N-thiomorpholinyl;
wherein any said alkylene group may be optionally substituted with one to three $R^{10}$ groups;

the other $R^3$, $R^4$, $R^5$, or $R^6$ moieties can be selected independently from H, halogen, $R^{10}$, OR$^{20}$, optionally substituted alkyl, optionally substituted alkenyl, and optionally substituted alkynyl, wherein said optional substituents are one to three $R^{10}$ groups;

Q is selected from an optionally substituted $C_{1-2}$ alkylene, wherein said optional substituents are one to three $R^{10}$ groups;

$R^{10}$ is selected from alkyl, aryl, heteroaryl, cycloalkyl, spirocycloalkyl, heterocycloalkyl, arylalkoxy, F, Cl, Br, I, CF$_3$, NR$^{31A}$R$^{31B}$, OR$^{30}$, OCF$_3$, O—Si(R$^{29}$)$_3$, O-tetrahydropyranyl, ethylene oxide, (CH$_2$)$_p$OR$^{30}$, OR$^{28}$, and a monosaccharide wherein each hydroxyl group of the monosaccharide is independently either unsubstituted or is replaced by H, alkyl, or alkoxy;

$R^{11}$ is selected from H and optionally substituted alkyl, wherein said optional substituents are one to three $R^{10}$ groups;

$R^{13}$ is independently selected from optionally substituted cycloalkyl, and optionally substituted heterocycloalkyl, wherein said optional substituents are one to three $R^{10}$ groups;

R[18] and R[19] are each independently selected from H, optionally substituted alkyl, optionally substituted aryl, optionally substituted heteroaryl, optionally substituted cycloalkyl, and optionally substituted heterocycloalkyl, wherein said optional substituents are one to three R[10] groups;

R[20] is selected from H, optionally substituted alkyl, optionally substituted alkenyl, optionally substituted alkynyl, optionally substituted aryl, optionally substituted arylalkyl, optionally substituted heteroaryl, optionally substituted cycloalkyl, and optionally substituted heterocycloalkyl, wherein said optional substituents are one to three R[10] groups;

R[22] is optionally substituted $C_5$-$C_{10}$ alkyl, wherein said optional substituents are one to three R[10] groups;

R[27] is selected from optionally substituted cycloalkyl, wherein said optional substituents are one to three R[10] groups;

R[28] is the residue of an amino acid after the removal of the hydroxyl moiety from the carboxyl group thereof;

R[29] is H or alkyl;

R[30] is H, alkyl, aryl, arylalkyl, heteroaryl, cycloalkyl, or heterocycloalkyl;

R[31A] and R[31B] are each independently selected from H, alkyl, and arylalkyl, or together with the nitrogen to which they are attached form a heterocycloalkyl;

R[32] is optionally substituted aryl, wherein said optional substituents are one to three R[10] groups;

R[33] is selected from optionally substituted cycloalkyl, optionally substituted heteroaryl, and optionally substituted heterocycloalkyl, wherein said optional substituents are one to three R[10] groups;

p is independently selected from 1, 2, 3, and 4;

x is 0 or 1;

or a stereoisomer or salt form thereof, said method comprising the steps of:
i) contacting said compound of formula (I) with a metal hydride together with an activating agent selected from a mineral, organic or Lewis acid in a solvent; and optionally
ii) recovering the obtained compound of formula (II).

In another aspect, the metal hydride is selected from an aluminium hydride, or a borohydride. As examples of aluminium hydride, mention may be made of dialkylaluminium hydride such as $iPr_2AlH$ or $iBu_2AlH$ (also called DIBAL-H), alkaline metal aluminium hydride such as $LiAlH_4$, $NaAlH_4$, $LiAlH(OAlk)_3$, $LiAlH(NH_2)_3$, $LiAlH(NAlk)_3$ or $LiAlH_2(OAlk)_2$, wherein Alk denotes a $C_1$-$C_6$ alkyl group. Examples of $LiAlH(OAlk)_3$ include notably $LiAlH(OEt)_3$. Examples of $LiAlH_2(NAlk)_2$ include notably $LiAlH_2(OEt)_2$.

As examples of borohydrides, mention may be made notably of $NaBH_4$, $NaBH_3CN$ or $LiHB(Alk)_3$, $NaHB(Alk)_3$, $KHB(Alk)_3$. Examples of $LiHB(Alk)_3$ include notably LiHB(sec-butyl) (also called L-selectride).

Preferably, the metal hydride is a borohydride, and most preferably $NaBH_4$.

In an additional aspect, the molar ratio of the reducing agent relative to the compound of formula (I) ranges from 1 to 30 equivalents.

In a further aspect, the activating agent is a Lewis acid, preferably selected from the group consisting of $MgCl_2$, $CaCl_2$, $CeCl_3$, $TiCl_4$, $MgCl_2$ being particularly preferred.

In another aspect, the molar ratio of the activating agent relative to the compound of formula (I) ranges from 0.1 to 10 equivalents, notably from 1 to 5 equivalents.

In a still further aspect, in step i), the metal hydride is added to the compound of formula (I) prior to the activating agent.

Preferably, the metal hydride is added to the compound of formula (I) at a temperature equal or inferior than −10° C. In a preferred embodiment, the temperature is maintained during a period of at least 1 hour before the reaction is allowed to stand at room temperature, i.e at a temperature of about 18-22° C. Indeed, it was observed that when adding the metal hydride to the compound of formula (I) at a low temperature, high regioselectivities were advantageously obtained along with high conversion rates.

In another aspect, ring B is a 5-membered aromatic ring in which one or two carbon atoms may be replaced with a nitrogen atom such as a pyrazolylene.

In a further aspect, $R^1$ is H.

In a still further aspect, $R^2$ is H.

In yet another aspect, Q is preferably $CH_2$ or $CH_2CH_2$.

In a further aspect, B ring is

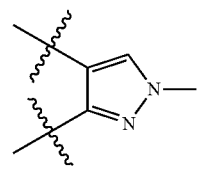 [SMILES: *c1cn(C)nc1*]

In a still further aspect, B ring is

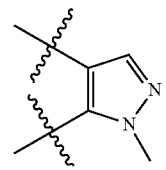 [SMILES: *c1cnn(C)c1*]

In another aspect, the compound of formula (II) has the general formula (IIa):

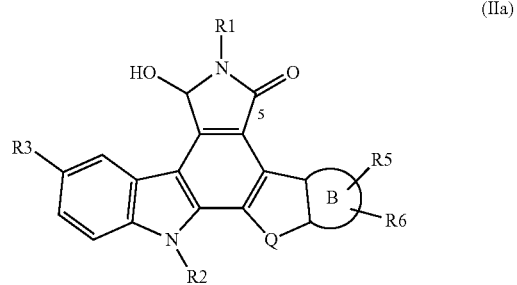

(IIa)

In a particular embodiment, the compound of formula (II) has the general formula (IIb):

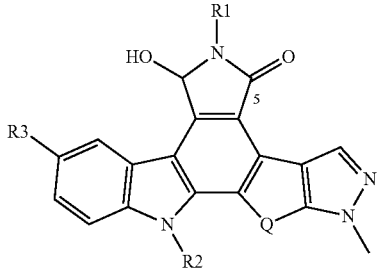
(IIb)

In another particular embodiment, the compound of formula (II) has the general formula (IIc):

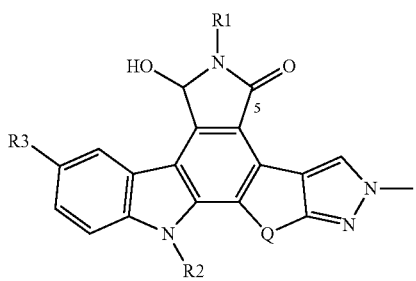
(IIc)

In a still particular embodiment, the compound of formula (II) is

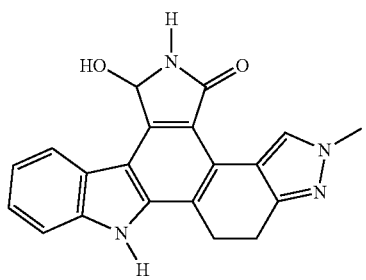
(IId)

In a further aspect, the invention provides a method for reducing a compound of formula (II) into a compound of formula (III):

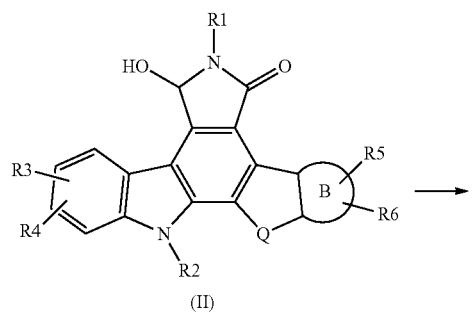
(II)

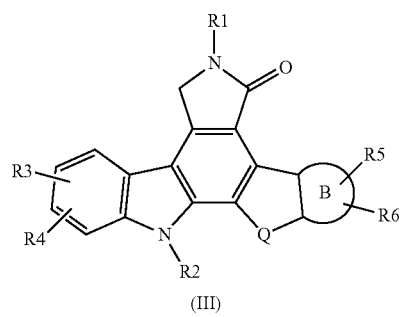
(III)

wherein B ring, Q, $R_1$, $R_2$, $R_3$, $R_4$, $R_5$ and $R_6$ are as defined herein, said method comprising the steps of:

i) reducing the alcohol function of said compound of formula (II); and optionally ii) recovering the obtained compound of formula (III).

In an additional aspect, the reduction is performed by contacting the compound of formula (II) with a reducing agent selected from $R_3SiH$ or $RSeH$ together with an activating agent selected from a mineral, organic or Lewis acid, wherein R is a $C_1$-$C_6$ alkyl or a $C_6$-$C_{10}$ aryl group.

In a further aspect, the reducing agent is $R_3SiH$, notably $Et_3SiH$.

In a still further aspect, the activating agent is a Lewis acid, preferably $BF_3$, $NH_4F$ or $tBu_4NF$.

In a preferred aspect, the reduction is performed in the presence of $Et_3SiH$ and $BF_3 \cdot Et_2O$.

In an another aspect, the compound of formula (II) is prepared according to the method defined herein.

In additional aspects of the present invention, the compound of formula (III) has the general formula (IIIa), (IIIb), or (IIIc):

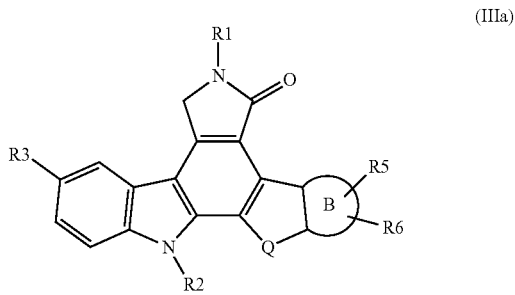
(IIIa)

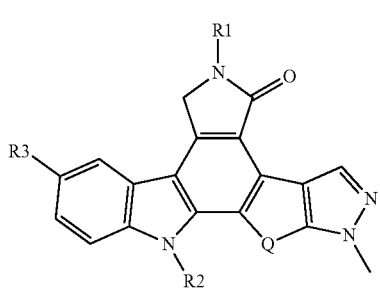
(IIIb)

-continued

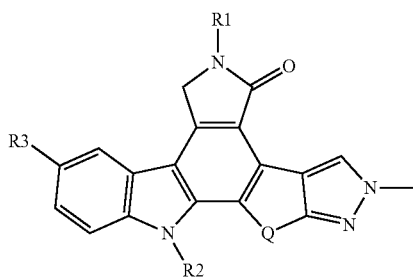
(IIIc)

In a preferred embodiment, the compound of formula (III) has the general formula (IIId):

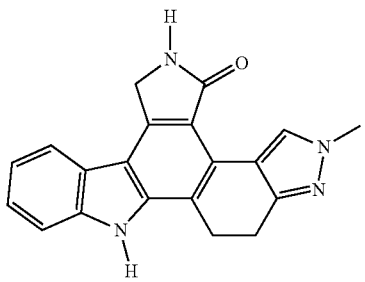
(IIId)

In a further aspect, the invention provides a use of a compound of formula (II) for preparing a compound of formula (III):

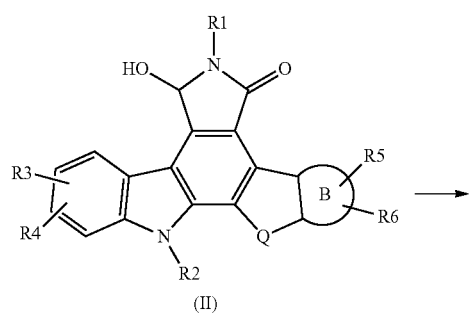
(II)

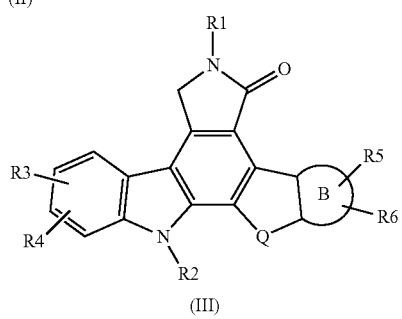
(III)

wherein B ring, Q, $R_1$, $R_2$, $R_3$, $R_4$, $R_5$ and $R_6$ are as defined herein.

In an additional aspect, the invention provides a use of a compound of formula (IId) for preparing a compound of formula (IV) or an acidic addition salt thereof:

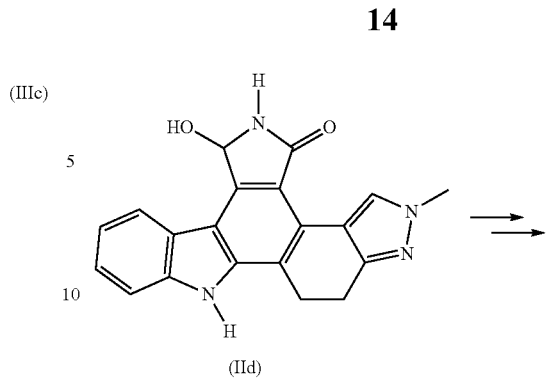
(IId)

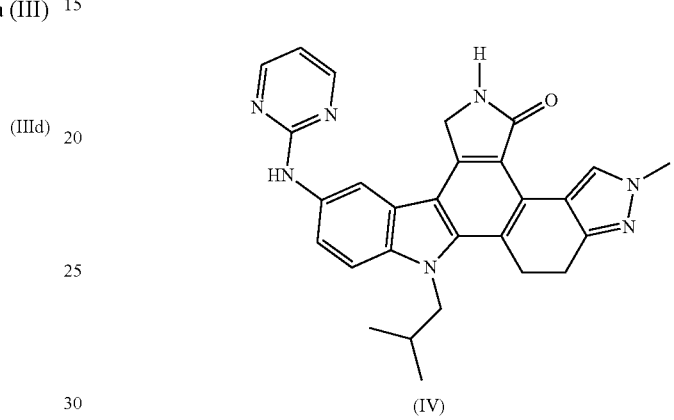
(IV)

In a further aspect, the invention provides a compound of formula (II):

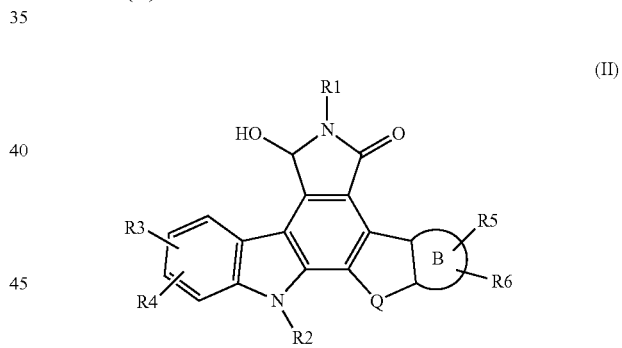
(II)

wherein B ring, Q and $R_1$, $R_2$, $R_3$, $R_4$, $R_5$ and $R_6$ are as defined herein.

In certain aspects of the present invention, there are included compounds of formula (II), wherein ring B is a 5-membered aromatic ring in which one or two carbon atoms may be replaced with a nitrogen atom, preferably a pyrazolylene, and most preferably:

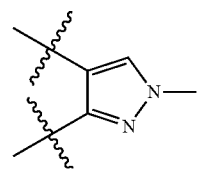 [SMILES: *c1cn(C)nc1*]

In another aspect of the invention, there are included compounds of formula (II) wherein B is:

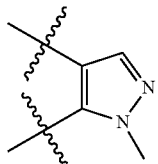 [SMILES: *c1cnn(C)c1*]

Other aspects of the present invention include compounds of Formula (II), wherein $R^1$ is H.

Still another aspect of the present invention includes compounds of Formula (II) wherein $R^2$ is H.

Yet another aspect of the present invention includes compounds of formula (II) wherein Q is optionally substituted $C_{1-2}$ alkylene, such as notably $CH_2$ or $CH_2CH_2$.

In a certain aspect of the invention, there are included compounds of formula (II) having the general formula (IIa):

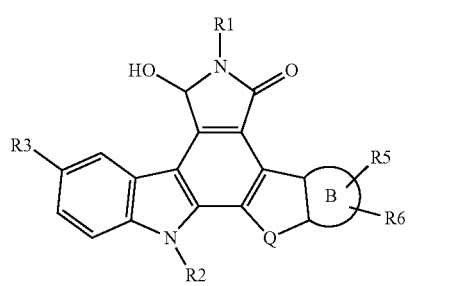
(IIa)

In a further aspect of the invention, there are included compounds of formula (II) having the general formula (IIb):

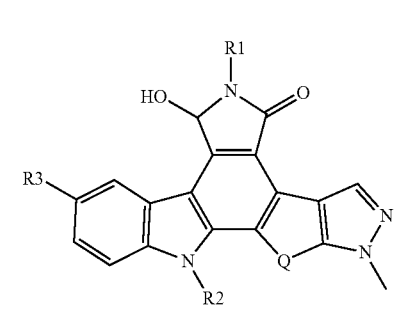
(IIb)

In a still further aspect of the invention, there are included compounds of formula (II) having the general formula (IIc):

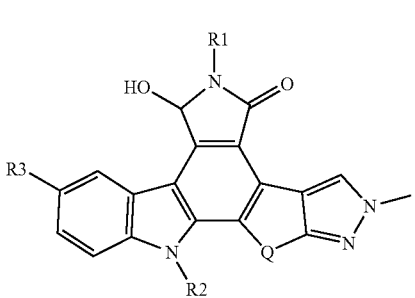
(IIc)

In a preferred aspect of the invention, the compound of formula (II) is:

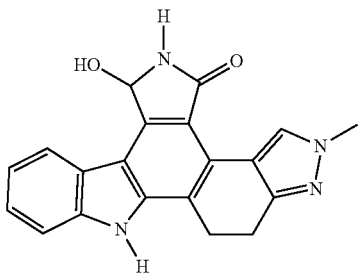
(IId)

The following terms and expressions used herein have the indicated meanings.

As used herein, the term "about" refers to a range of values from ±10% of a specified value. For example, the phrase "about 50 mg" includes ±10% of 50, or from 45 to 55 mg.

As used herein, a range of values in the form "x-y" or "x to y", or "x through y", include integers x, y, and the integers therebetween. For example, the phrases "1-6", or "1 to 6" or "1 through 6" are intended to include the integers 1, 2, 3, 4, 5, and 6. Preferred embodiments include each individual integer in the range, as well as any subcombination of integers. For example, preferred integers for "1-6" can include 1, 2, 3, 4, 5, 6, 1-2, 1-3, 1-4, 1-5, 2-3, 2-4, 2-5, 2-6, etc.

As used herein, the term "alkyl" refers to a straight-chain, or branched alkyl group having 1 to 8 carbon atoms, such as methyl, ethyl, propyl, isopropyl, butyl, isobutyl, sec-butyl, tert-butyl, pentyl, isoamyl, neopentyl, 1-ethylpropyl, 3-methylpentyl, 2,2-dimethylbutyl, 2,3-dimethylbutyl, hexyl, octyl, etc. The alkyl moiety of alkyl-containing groups, such as alkoxy, alkoxycarbonyl, and alkylaminocarbonyl groups, has the same meaning as alkyl defined above. Lower alkyl groups, which are preferred, are alkyl groups as defined above which contain 1 to 4 carbons. A designation such as "$C_1$-$C_4$ alkyl" refers to an alkyl radical containing from 1 to 4 carbon atoms.

As used herein, the term "alkenyl" refers to a straight chain, or branched hydrocarbon chains of 2 to 8 carbon atoms having at least one carbon-carbon double bond. A designation "$C_2$-$C_8$ alkenyl" refers to an alkenyl radical containing from 2 to 8 carbon atoms. Examples of alkenyl groups include notably ethenyl, propenyl, isopropenyl, 2,4-pentadienyl.

As used herein, the term "alkynyl" refers to a straight chain, or branched hydrocarbon chains of 2 to 8 carbon atoms having at least one carbon-carbon triple bond. A designation "$C_2$-$C_8$ alkynyl" refers to an alkynyl radical containing from 2 to 8 carbon atoms. Examples include notably ethynyl, propynyl, isopropynyl, 3,5-hexadiynyl.

As used herein, the term "alkylene" refers to a branched or straight chained hydrocarbon of 1 to 8 carbon atoms, which is formed by the removal of two hydrogen atoms. A designation such as "$C_1$-$C_4$ alkylene" refers to an alkylene radical containing from 1 to 4 carbon atoms. Examples include methylene (—$CH_2$—), propylidene ($CH_3CH_2CH$=), 1,2-ethandiyl (—$CH_2CH_2$—), etc.

As used herein, the term "phenylene" refers to a phenyl group with an additional hydrogen atom removed, ie. a moiety with the structure of:

As used herein, the terms "carbocycle", "carbocyclic" or "carbocyclyl" refer to a stable, saturated or partially saturated, monocyclic or bicyclic hydrocarbon ring system which is saturated, partially saturated or unsaturated, and contains from 3 to 10 ring carbon atoms. Accordingly the carbocyclic group may be aromatic or non-aromatic, and includes the cycloalkyl and aryl groups defined herein. The bonds connecting the endocyclic carbon atoms of a carbocyclic group may be single, double, triple, or part of a fused aromatic moiety.

As used herein, the term "cycloalkyl" refers to a saturated or partially saturated mono- or bicyclic alkyl ring system containing 3 to 10 carbon atoms. A designation such as "$C_5$-$C_7$ cycloalkyl" refers to a cycloalkyl radical containing from 5 to 7 ring carbon atoms. Preferred cycloalkyl groups include those containing 5 or 6 ring carbon atoms. Examples of cycloalkyl groups include notably cyclopropyl, cyclobutyl, cyclopentyl, cyclohexyl, cyclohexenyl, cycloheptyl, cyclooctyl.

As used herein, the term "spirocycloalkyl" refers to a cycloalkyl group bonded to a carbon chain or carbon ring moiety by a carbon atom common to the cycloalkyl group and the carbon chain or carbon ring moiety. For example, a $O_3$ alkyl group substituted with an R group wherein the R group is spirocycloalkyl containing 5 carbon atoms refers to:

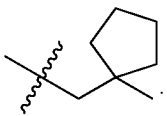 [SMILES: *CC1(C)CCCC1]

As used herein, the term "aryl" refers to a mono- or bicyclic hydrocarbon aromatic ring system having 6 to 12 ring carbon atoms. Examples include phenyl and naphthyl. Preferred aryl groups include phenyl or naphthyl groups. Included within the definition of "aryl" are fused ring systems, including, for example, ring systems in which an aromatic ring is fused to a cycloalkyl ring. Examples of such fused ring systems include, for example, indane and indene.

As used herein, the terms "heterocycle", "heterocyclic" or "heterocyclyl" refer to a mono- di-, tri- or other multicyclic aliphatic ring system that includes at least one heteroatom such as O, N, or S. The nitrogen and sulfur heteroatoms may be optionally oxidized, and the nitrogen may be optionally substituted in non-aromatic rings. Heterocycles are intended to include heteroaryl and heterocycloalkyl groups.

Some heterocyclic groups containing one or more nitrogen atoms include pyrrolidine, pyrroline, pyrazoline, piperidine, morpholine, thiomorpholine, N-methylpiperazine, indole, isoindole, imidazole, imidazoline, oxazoline, oxazole, triazole, thiazoline, thiazole, isothiazole, thiadiazole, triazine, isoxazole, oxindole, pyrazole, pyrazolone, pyrimidine, pyrazine, quinoline, iosquinoline, and tetrazole groups. Some heterocyclic groups formed containing one or more oxygen atoms include furan, tetrahydrofuran, pyran, benzofurans, isobenzofurans, and tetrahydropyran groups. Some heterocyclic groups containing one or more sulfur atoms include thiophene, thianaphthene, tetrahydrothiophene, tetrahydrothiapyran, and benzothiophenes.

As used herein, the term "heterocycloalkyl" refers to a cycloalkyl group in which one or more ring carbon atoms are replaced by at least one hetero atom such as —O—, —N—, or —S—, and includes ring systems which contain a saturated ring group bridged or fused to one or more aromatic groups. Some heterocycloalkyl groups containing both saturated and aromatic rings include phthalamide, phthalic anhydride, indoline, isoindoline, tetrahydroisoquinoline, chroman, isochroman, and chromene.

As used herein, the term "heteroaryl" refers to an aryl group containing 5 to 10 ring carbon atoms in which one or more ring carbon atoms are replaced by at least one hetero atom such as —O—, —N—, or —S—. Some heteroaryl groups of the present invention include pyridyl, pyrimidyl, pyrrolyl, furanyl, thienyl, imidazolyl, triazolyl, tetrazolyl, quinolyl, isoquinolyl, benzoimidazolyl, thiazolyl, pyrazolyl, and benzothiazolyl groups.

As used herein, the term "arylalkyl" refers to an alkyl group that is substituted with an aryl group. Examples of arylalkyl groups include, but are not limited to, benzyl, phenethyl, benzhydryl, diphenylmethyl, triphenylmethyl, diphenylethyl, naphthylmethyl.

As used herein, the term "heteroarylalkyl" refers to an alkyl group that is substituted with a heteroaryl group.

As used herein, the term "alkoxy" refers to an oxygen radical substituted with an alkyl group. Examples include notably methoxy, ethoxy, n-propoxy, isopropoxy, n-butoxy, isobutoxy, sec-butoxy, t-butoxy.

As used herein, the term "arylalkoxy" refers to an aryl-substituted alkoxy group, such as benzyloxy, diphenylmethoxy, triphenylmethoxy, phenylethoxy, diphenylethoxy.

As used herein, the term "alkylcarbonyloxy" refers to an $R^C(=O)O$— group, wherein R is an alkyl group.

As used herein, the term "monosaccharide" refers to a simple sugar of the formula $(CH_2O)_n$. The monosaccharides can be straight-chain or ring systems, and can include a saccharose unit of the formula —CH(OH)—C(=O)—. Examples of monosaccharides include erythrose, threose, ribose, arabinose, xylose, lyxose, allose, altrose, glucose, mannose, gulose, idose, galactose, talose, erythulose, ribulose, xyulose, psicose, fructose, sorbose, tagatose, erythropentulose, threopentulose, glycerotetrulose, glucopyranose, fructofuranose, etc.

As used herein, the term "amino acid" refers to a group containing both an amino group and a carboxyl group. Embodiments of amino acids include α-amino, β-amino, γ-amino acids. The α-amino acids have a general formula HOOC—CH(side chain)-$NH_2$. The amino acids can be in their D, L or racemic configurations. Amino acids include naturally-occurring and non-naturally occurring moieties. The naturally-occurring amino acids include the standard 20 α-amino acids found in proteins, such as glycine, serine, tyrosine, proline, histidine, glutamine, etc. Naturally-occurring amino acids can also include non-α-amino acids (such as β-alanine, γ-aminobutyric acid, homocysteine, etc.), rare amino acids (such as 4-hydroxyproline, 5-hydroxylysine, 3-methylhistidine, etc.) and non-protein amino acids (such as citrulline, ornithine, canavanine, etc.). Non-naturally occurring amino acids are well-known in the art, and include analogs of natural amino acids. See Lehninger, A. L. *Biochemistry*, 2$^{nd}$ ed.; Worth Publishers: New York, 1975; 71-77, the disclosure of which is incorporated herein by reference. Non-naturally occurring amino acids also include α-amino acids wherein the side chains are replaced with synthetic derivatives. In certain embodiments, substituent groups for the compounds of the present invention include the residue of an amino acid after removal of the hydroxyl moiety of the carboxyl group thereof; i.e., groups of formula —C(=O)CH (side chain)-NH$_2$. Representative side chains of naturally occurring and non-naturally occurring α-amino acids include are shown below in Table A.

TABLE A

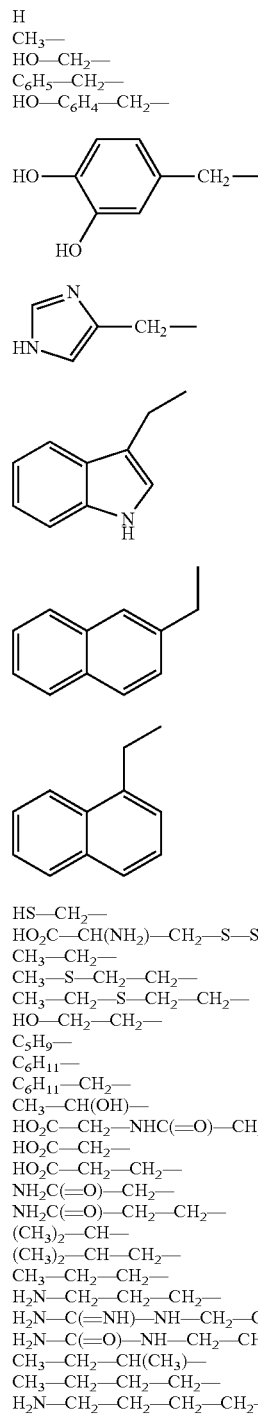

H
CH$_3$—
HO—CH$_2$—
C$_6$H$_5$—CH$_2$—
HO—C$_6$H$_4$—CH$_2$—

HS—CH$_2$—
HO$_2$C—CH(NH$_2$)—CH$_2$—S—S—CH$_2$—
CH$_3$—CH$_2$—
CH$_3$—S—CH$_2$—CH$_2$—
CH$_3$—CH$_2$—S—CH$_2$—CH$_2$—
HO—CH$_2$—CH$_2$—
C$_5$H$_9$—
C$_6$H$_{11}$—
C$_6$H$_{11}$—CH$_2$—
CH$_3$—CH(OH)—
HO$_2$C—CH$_2$—NHC(=O)—CH$_2$—
HO$_2$C—CH$_2$—
HO$_2$C—CH$_2$—CH$_2$—
NH$_2$C(=O)—CH$_2$—
NH$_2$C(=O)—CH$_2$—CH$_2$—
(CH$_3$)$_2$—CH—
(CH$_3$)$_2$—CH—CH$_2$—
CH$_3$—CH$_2$—CH$_2$—
H$_2$N—CH$_2$—CH$_2$—CH$_2$—
H$_2$N—C(=NH)—NH—CH$_2$—CH$_2$—CH$_2$—
H$_2$N—C(=O)—NH—CH$_2$—CH$_2$—CH$_2$—
CH$_3$—CH$_2$—CH(CH$_3$)—
CH$_3$—CH$_2$—CH$_2$—CH$_2$—
H$_2$N—CH$_2$—CH$_2$—CH$_2$—CH$_2$—

As used herein, the term "trk" refers to the family of high affinity neurotrophin receptors presently comprising trk A, trk B, and trk C, and other membrane associated proteins to which a neurotrophin can bind.

It is recognized that compounds of the present invention may exist in various stereoisomeric forms. As such, the compounds of the present invention include their respective enantiomers. The compounds are normally prepared as racemates and can conveniently be used as such, but individual enantiomers can be isolated or synthesized by conventional techniques if so desired. Such racemates and individual enantiomers and mixtures thereof form part of the present invention.

It is further recognized that functional groups present on the compounds of the present invention may contain protecting groups. Protecting groups are known per se as chemical functional groups that can be selectively appended to and removed from functionalities, such as hydroxyl groups and carboxyl groups. These groups are present in a chemical compound to render such functionality inert to chemical reaction conditions to which the compound is exposed. Any of a variety of protecting groups may be employed with the present invention. Preferred groups for protecting lactams include silyl groups such as t-butyldimethylsilyl ("TBDMS"), dimethoxybenzhydryl ("DMB"), acyl, benzyl ("Bn"), and methoxybenzyl groups. Preferred groups for protecting hydroxy groups include TBS, acyl, benzyl, benzyloxycarbonyl ("CBZ"), t-butyloxycarbonyl ("Boc"), and methoxymethyl. Many other standard protecting groups employed by one skilled in the art can be found in Greene, T. W. and Wuts, P. G. M., "Protective Groups in Organic Synthesis" 2d. Ed., Wiley & Sons, 1991.

EXAMPLES

Other features of the invention will become apparent in the course of the following descriptions of exemplary embodiments. These examples are given for illustration of the invention and are not intended to be limiting thereof.

I.—Regioselective Reduction of Maleimide Compound into C7 Hydroxy Lactam Regioisomer General Procedure

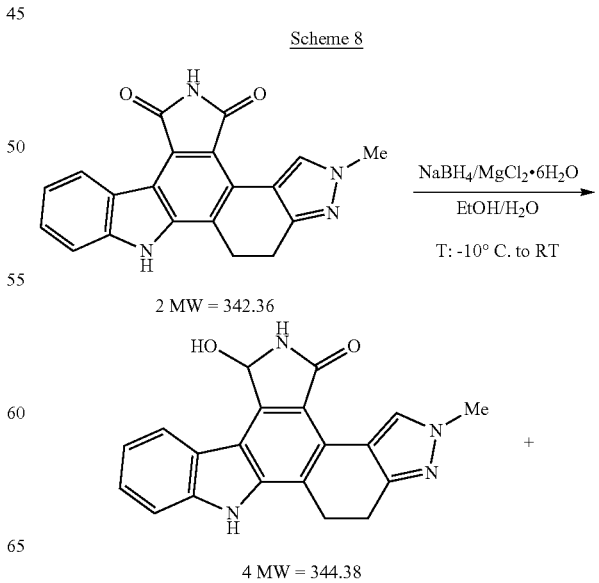

-continued

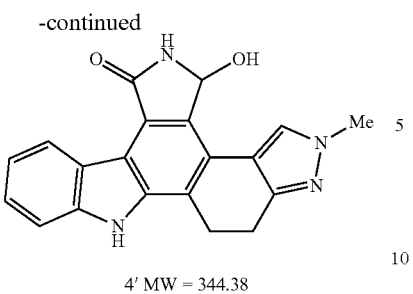

4' MW = 344.38

| Name | Quality | Eq/volume | Properties | Moles |
|---|---|---|---|---|
| Maleimide 2 | | 1.00 eq | M = 342.36 | $2.92\ 10^{-3}$ |
| Sodium tetrahydruroborate (NaBH$_4$) | 99% | 1.05 eq | M = 37.83 | $2.92\ 10^{-3}$ |
| Magnesium chloride hexahydrate | | 0.20 to 1.05 eq | M = 203.31 | $0.58\ 10^{-3}$ |
| Ethanol | absolute | 7 to 30 vol | bp 78° C. | |
| Water | HPLC | 1.3 vol | | |

In a three bottom flask equipped with a magnetic stirrer and a thermometer:

1) preparing a suspension of maleimide 2 in absolute ethanol, 2) cooling the suspension at a temperature inferior or equal to −10° C. by the means of a bath of iced water/acetone, 3) adding 1.05 eq of sodium tetrahydruroborate (NaBH$_4$) in one portion, 4) adding drop by drop an aqueous solution of magnesium chloride, 5) stirring the reactive mixture at a temperature inferior or equal to −10° C. in a first time and monitoring the progress of the reaction by HPLC, 6) then stirring the reactive mixture at room temperature (RT): as the progress of the reaction is monitored by HPLC, NaBH$_4$ can be added to improve the conversion of maleimide 2.

When the reaction is finished, the excess of NaBH$_4$ is destroyed before filtering, washing and drying the isolated product.

HPLC conditions for the reaction monitoring and the control of the isolated product:

Column: X-Terra MS C18 (150×4.6 mm, 5 μm)
Detector: UV à 225 nm, 270 nm, 277 nm, 290 nm
Oven temperature: 30° C.
Flow: 1.0 mL.min$^{-1}$
Injected volume: 10 μL
Eluent and gradient:

| Time (min) | CH$_3$COONH$_4$ 10 mM in H$_2$O | CH$_3$COONH$_4$ 10 mM in MeOH(50)/CH$_3$CN(50) |
|---|---|---|
| 0 | 70 | 30 |
| 11 | 40 | 60 |
| 15 | 40 | 60 |
| 23 | 15 | 85 |
| 23.1 | 70 | 30 |
| 27 | 70 | 30 |

Results:
Retention time for compound 4': 8.0 min.
Retention time for compound 4: 8.3 min.
Retention time for compound 2: 13.3 min.

The relative proportion of regioisomers 4 and 4' may be assessed by comparing their respective UV spectra at 290 nm.

A.—Maleimide 2, Reductive Agent (NaBH$_4$) and Activating Agent (MgCl$_2$.6H$_2$O) in Stoechiometric Ratios Example 1

| Initial mass (g) | Product | Mass obtained (g) |
|---|---|---|
| 1.50 | 2, 4 & 4' | 2.25 |

In a three bottom flask equipped with a magnetic stirrer and a thermometer, the following steps were performed:

1) preparing a suspension of maleimide 2 (1.50 g) in 7 vol of absolute ethanol, 2) cooling the suspension at a temperature inferior or equal to −10° C. by the means of a bath of iced water/acetone, 3) adding 1.05 eq of sodium tetrahydruroborate (NaBH$_4$) in one portion, 4) adding drop by drop an aqueous solution of 1.05 eq of magnesium chloride in 2 mL of water, 5) stirring the reactive mixture at a temperature inferior or equal to −5° C. in a first time and monitoring the progress of the reaction by HPLC: the kinetic of the reaction was slow so that a supplemental portion (3.15 eq) of NaBH$_4$ was added during 9 hours of stirring. The kinetic of the reaction was still slow as shown on the table below (HPLC analysis at $\lambda$=290 nm after 6 hours of reaction):

| Retention time X-terra (min) | Structural correspondence | % Area ($\lambda$ = 290 nm) | Relative proportion |
|---|---|---|---|
| 8.0 | 4' | 8.1 | 18 |
| 8.3 | 4 | 38.0 | 82 |
| 13.3 | 2 | 45.1 | |

6) the reactive mixture was then stirred at room temperature (RT): after 4 days of stirring, the HPLC analysis at $\lambda$=290 nm was as follows:

| Retention time X-terra (min) | Structural correspondence | % Area ($\lambda$ = 290 nm) | Relative proportion |
|---|---|---|---|
| 8.0 | 4' | 13.8 | 20 |
| 8.3 | 4 | 55.0 | 80 |
| 13.3 | 2 | 30.5 | |

A large amount of water was added, then the reactive mixture was filtered washed, dried and analyzed by HPLC (m obtained=2.25 g):

| Retention time X-terra (min) | Structural correspondence | % Area ($\lambda$ = 290 nm) | Relative proportion |
|---|---|---|---|
| 8.0 | 4' | 7.2 | 10 |
| 8.3 | 4 | 67.8 | 90 |
| 13.3 | 2 | 23.9 | |

Example 2

| Initial mass (g) | Product | Mass obtained (g) |
|---|---|---|
| 1.50 | 2, 4 & 4' | 1.58 |

In a three bottom flask equipped with a magnetic stirrer and a thermometer, the following steps were performed:

1) preparing a suspension of maleimide 2 (1.50 g) in 7 vol of absolute ethanol,
2) cooling the suspension at a temperature inferior or equal to −10° C. by the means of a iced water bath/acetone,
3) adding 1.05 eq of sodium tetrahydruroborate ($NaBH_4$) in one portion,
4) adding drop by drop an aqueous solution of 1.05 eq of magnesium chloride in 2 mL of water,
5) stirring the reactive mixture at a temperature inferior or equal to −5° C. and monitoring the progress of the reaction by HPLC at that temperature: the kinetic of the reaction was slow so that a supplemental portion (4.20 esq.) of $NaBH_4$ was added during 7 hours of stirring. The kinetic of the reaction was still slow as shown on the table below (HPLC analysis at $\lambda$=290 nm after 5 hours of reaction):

| Retention time X-terra (min) | Structural correspondence | % Area ($\lambda$ = 290 nm) | Relative Proportion |
|---|---|---|---|
| 8.1 | 4' | 7.6 | 17.4 |
| 8.4 | 4 | 36.0 | 82.6 |
| 13.3 | 2 | 54.8 | |

A large amount of water was added, then the reactive mixture was filtered washed, dried and analyzed by HPLC (m obtained=1.58 g):

Example 3

| Initial mass (g) | Product | Mass obtained (g) |
|---|---|---|
| 1.50 | 2, 4 & 4' | Not isolated |

In a three bottom flask equipped with a magnetic stirrer and a thermometer, the following steps were performed:

1) preparing a suspension of maleimide 2 (1.50 g) in 7 vol of absolute ethanol,
2) cooling the suspension at a temperature inferior or equal to −10° C. by the means of a iced water bath/acetone,
3) adding 1.05 eq of sodium tetrahydruroborate ($NaBH_4$) in one portion,
4) adding drop by drop an aqueous solution of 1.05 eq of magnesium chloride in 2 mL of water,
5) stirring the reactive mixture at a temperature inferior or equal to −5° C. and monitoring the progress of the reaction by HPLC at that temperature: the kinetic of the reaction was slow so that a supplemental portion (4.20 eq) of $NaBH_4$ was added during 6 to 7 hours;
6) the reactive mixture was then stirred at room temperature (RT): after 20 days of stirring and addition of a supplemental amount of $NaBH_4$ (6.30 eq) in 10 vol of ethanol, the HPLC analysis at $\lambda$=290 nm was as follows:

| Retention time X-terra (min) | Structural correspondence | % Area ($\lambda$ = 290 nm) | Relative proportion |
|---|---|---|---|
| 8.0 | 4' | 17.0 | 20 |
| 8.3 | 4 | 66.7 | 80 |
| 13.3 | 2 | 14.2 | |

The reactive mixture was not worked up.

B.—Amendment of the General Procedure: Activating Agent ($MgCl_2.6H_2O$) in Catalytic Amount

Example 4

| Initial mass (g) | product | Mass obtained (g) |
|---|---|---|
| 1.50 | 2, 4 & 4' | 1.26 |

In a three bottom flask equipped with a magnetic stirrer and a thermometer, the following steps were performed:

1) preparing a suspension of maleimide 2 (1.50 g) in 7 vol of absolute ethanol,
2) cooling the suspension at a temperature inferior or equal to −10° C. by the means of a iced water bath/acetone,
3) adding 1.05 eq of sodium tetrahydruroborate ($NaBH_4$) in one portion,
4) adding drop by drop an aqueous solution of 0.20 eq of magnesium chloride in 0.4 mL of water,
5) stirring the reactive mixture at a temperature inferior or equal to −5° C. and monitoring the progress of the reaction by HPLC at that temperature: the kinetic of the reaction was slow so that a supplemental portion (4.20 eq) of $NaBH_4$ was added during 6 hours: the progress of the reaction was slow. The HPLC analysis at $\lambda$=290 nm is reported in the table below:

| Retention time X-terra (min) | Structural correspondence | % Area ($\lambda$ = 290 nm) | Relative proportion |
|---|---|---|---|
| 8.0 | 4' | 3.0 | 14.2 |
| 8.3 | 4 | 18.4 | 85.8 |
| 13.3 | 2 | 73.1 | |

6) the reactive mixture was then stirred at room temperature (RT): after 13 days of stirring with addition of a supplemental amount of $NaBH_4$ (10.5 eq) in 7 vol of ethanol, the HPLC analysis at $\lambda$=290 nm was as follows:

| Retention time X-terra (min) | Structural correspondence | % Area ($\lambda$ = 290 nm) | Relative proportion |
|---|---|---|---|
| 8.0 | 4' | 9.3 | 10.6 |
| 8.3 | 4 | 78.0 | 89.4 |
| 13.3 | 2 | 9.8 | |

A large amount of water was added, then the reactive mixture was filtered washed, dried and analyzed by HPLC (m obtained=1.26 g):

| Retention time X-terra (min) | Structural correspondence | % Area (λ = 290 nm) | Relative proportion |
|---|---|---|---|
| 8.1 | 4' | 7.9 | 9 |
| 8.4 | 4 | 81.6 | 91 |
| 13.3 | 2 | 8.6 | |

II.—Reduction of $C_7$ Hydrox Lactam Regioisomer into the Corresponding Lactam

This reduction step is illustrated by the following scheme:

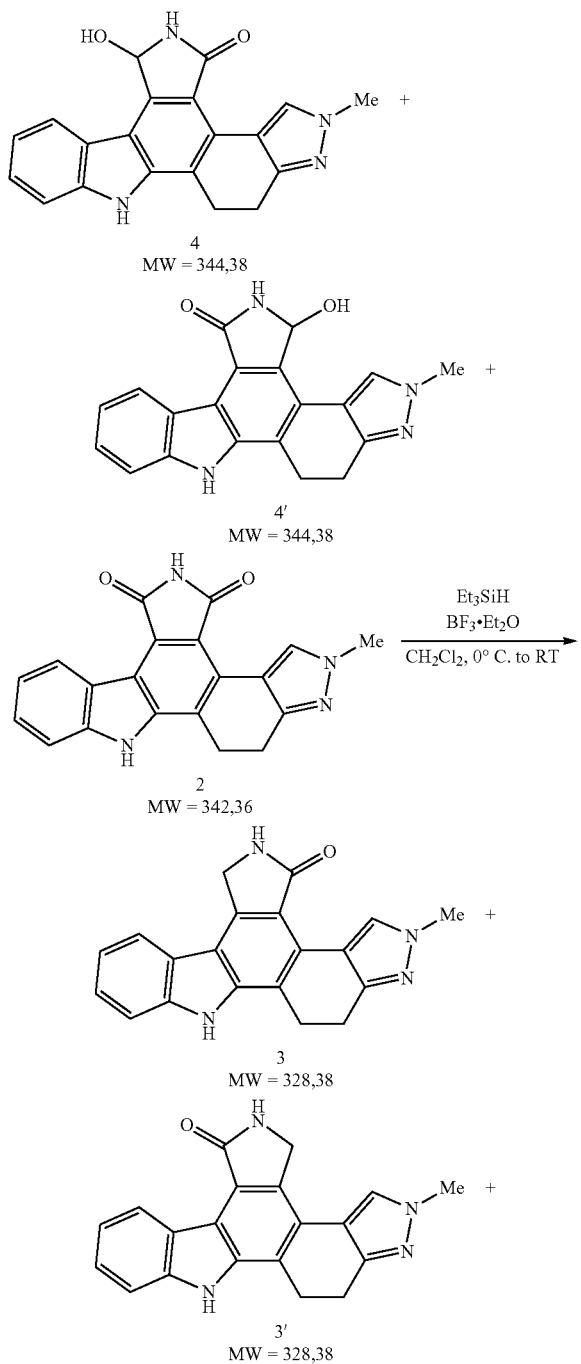

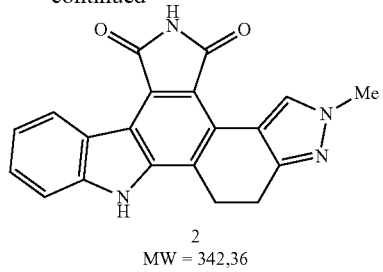

| Name | Quality | Eq/volume | Properties | Moles |
|---|---|---|---|---|
| Mixture composed of Hydroxy lactams 4 & 4' and of Maleimide 2 | | 1.00 eq | M = 344.38 | $1.09\ 10^{-3}$ |
| Triethylsilane (Et$_3$SiH) | 99% | 2.00 eq | M = 116.28 | $2.18\ 10^{-3}$ |
| Boron trifluoride diethyl etherate (BF$_3 \cdot$Et$_2$O) | | 2.00 eq | M = 141.93 | $2.18\ 10^{-3}$ |
| Dichloromethane | | 32 vol | bp 39-40° C. | |

General Procedure

In a dried three bottom flask, equipped with a magnetic stirrer and with a thermometer, the following steps were performed:

1. preparing a solution of hydroxyl lactam 4 and 4' and of maleimide 2, prepared according to par. I hereabove, in dichloromethane, under nitrogen atmosphere;

2. cooling the solution down to 0° C. by the mean of a iced water bath;

3. adding dropwise 2.00 eq of triethylsilane (Et$_3$SiH);

4. adding drop by drop 2.00 eq of boron trifluoride diethyl etherate (BF$_3$.Et$_2$O);

5. stirring the reactive mixture at 0° C. during 5 minutes in a first time;

6. allowing the temperature to rise and to stand at room temperature while monitoring the progress of the reaction by HPLC analysis.

HPLC Analytical Conditions for the Monitoring of the Reaction Progress and the Control of Isolated Product:

Column: X-Terra MS C18 (150×4.6 mm, 5 μm)

Detector: UV at 225 nm, 270 nm, 277 nm, 290 nm

Oven temperature: 30° C.

Flow: 1.0 mL.min$^{-1}$

Injected volume: 10 μL

Eluent and gradient:

| Time (min) | CH$_3$COONH$_4$ 10 mM in H$_2$O | CH$_3$COONH$_4$ 10 mM in MeOH(50)/CH$_3$CN(50) |
|---|---|---|
| 0 | 70 | 30 |
| 11 | 40 | 60 |
| 15 | 40 | 60 |
| 23 | 15 | 85 |
| 23.1 | 70 | 30 |
| 27 | 70 | 30 |

Results:

| Retention time X-terra (min) | Structural correspondence LC-MS |
|---|---|
| 8.0 | 4' |
| 8.3 | 4 |
| 9.4 | 3' |
| 11.0 | 3 |
| 13.3 | 2 |

Determination of Relative Ratios:

The comparison of UV spectra of compounds 3 ($t_R$=11.0 nm) and 3' ($t_R$=9.4 nm) and of maleimide 2 did not allow to exactly assess the relative ratio of each compound.

The relative ratio of lactams 3 and 3' ($t_R$=11.0 & 9.4 nm) was estimated by comparing the HPLC values measured at $\lambda$=277 nm, the relative ratio of maleimide ($t_R$=13.3 nm) being minimized.

Example 5

| Initial mass | Product | Mass obtained (g) |
|---|---|---|
| 0.50 | 3, 3', 4, 4', 2 & by-products | 0.30 |

In a dried three bottom flask, equipped with a magnetic stirrer and with a thermometer, the following steps were performed:
1) preparing a solution of hydroxyl lactam 4 and 4' and of maleimide (0.50 g of mixture in which the ratio of 4 & 4' is about 75%) in dicholoromethane (16 ml), under nitrogen atmosphere;
2) cooling the solution down to 0° C. by means of an iced water bath;
3) adding dropwise 2.00 eq of triethylsilane (Et$_3$SiH),
4) adding drop by drop 2.00 eq of boron trifluoride diethyl etherate (BF$_3$.Et$_2$O),
5) stirring the reactive mixture at 0° C. during 15 minutes in a first time,
6) allowing the temperature to rise and to stand at room temperature while monitoring the progress of the reaction by HPLC analysis.

HPLC analysis $\lambda$=277 nm after 24 h of stirring:

| Retention time X-terra (min) | Structural correspondence | % Area ($\lambda$ = 277 nm) | Relative proportion |
|---|---|---|---|
| 8.1 | 4' | 3.8 | |
| 8.4 | 4 | 4.9 | |
| 9.4 | 3' | 1.4 | 2.9 |
| 11.1 | 3 | 46.9 | 97.1 |
| 13.3 | 2 | 36.6 | |

HLPC analysis $\lambda$=277 nm after 45 h of stirring:

| Retention time X-terra (min) | Structural correspondence | % Area ($\lambda$ = 277 nm) | Relative proportion |
|---|---|---|---|
| 8.1 | 4' | — | |
| 8.4 | 4 | — | |
| 9.4 | 3' | 1.5 | 2.9 |
| 11.1 | 3 | 51.2 | 97.1 |
| 13.3 | 2 | 31.0 | |

The reaction was complete.

The reactive mixture was then neutralized by adding 5 ml of potassium carbonate (K$_2$CO$_3$) saturated aqueous solution, filtered. The product thus isolated was washed, dried and analysed by HPLC: m obtained=0.30 g

| Retention time X-terra (min) | Structural correspondence | % Area ($\lambda$ = 277 nm) | Relative proportion |
|---|---|---|---|
| 8.1 | 4' | 2.4 | |
| 8.4 | 4 | 4.2 | |
| 9.4 | 3' | 1.0 | 1.8 |
| 11.1 | 3 | 55.9 | 98.2 |
| 13.3 | 2 | 32.5 | |

After work up and drying, only minor amounts of hydroxyl lactam regioisomers 4' (2.4% at $\lambda$=277 nm) & 4 (4.2% at $\lambda$=277 nm).

The relative ratio of lactams 3'/3 at $\lambda$=277 nm is of 1.8/98.2.

The invention claimed is:

1. A method for regioselectively reducing a compound of formula (I) into a compound of formula (II):

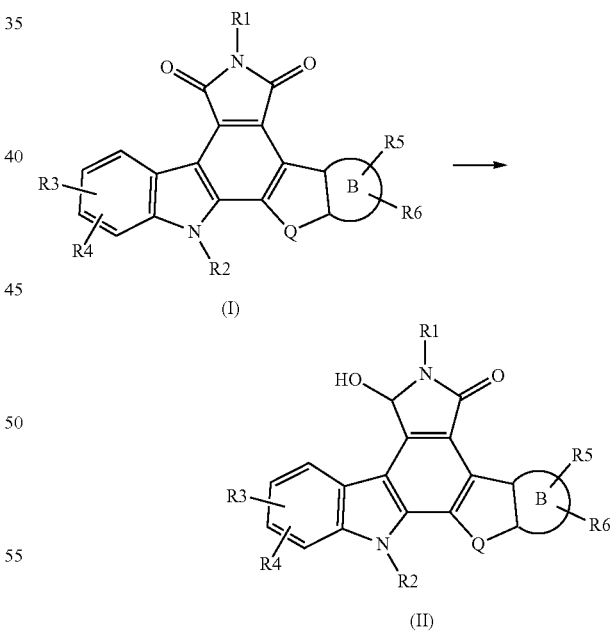

wherein:
ring B, together with the carbon atoms to which it is attached, is selected from:
(a) a phenylene ring in which from 1 to 3 carbon atoms may be replaced by nitrogen atoms; and
(b) a 5-membered aromatic ring in which either
(1) one carbon atom may be replaced with an oxygen, nitrogen, or sulfur atom;

(2) two carbon atoms may be replaced with a sulfur and a nitrogen atom, an oxygen and a nitrogen atom, or two nitrogen atoms; or (3) three carbon atoms may be replaced with three nitrogen atoms, one oxygen and two nitrogen atoms, or one sulfur and two nitrogen atoms;

$R^1$ and $R^2$ are each independently selected from H, optionally substituted alkyl, optionally substituted alkenyl, optionally substituted alkynyl, optionally substituted cycloalkyl, and optionally substituted heterocycloalkyl, wherein said optional substituents are one to three $R^{10}$ groups;

at least one of $R^3$, $R^4$, $R^5$, and $R^6$ is selected from H, $(alkylene)_xOR^{13}$, $(CH_2)_pOR^{22}$, O-(alkylene)-$R^{27}$, OCH$[(CH_2)_pOR^{20}]_2$, $NR^{11}R^{32}$, $NR^{11}R^{33}$, (alkylene)-$NR^{18}R^{19}$, substituted alkyl, wherein one of the substituents is a spirocycloalkyl group, optionally substituted $(alkylene)_x$-cycloalkyl, and optionally substituted-$(alkylene)_x$-heterocycloalkyl, wherein the heterocycloalkyl does not include unsubstituted N-morpholinyl, N-piperidyl, or N-thiomorpholinyl;

wherein any said alkylene group may be optionally substituted with one to three $R^{10}$ groups;

the other $R^3$, $R^4$, $R^5$, or $R^6$ moieties can be selected independently from H, halogen, $R^{10}$, $OR^{20}$, optionally substituted alkyl, optionally substituted alkenyl, and optionally substituted alkynyl, wherein said optional substituents are one to three $R^{10}$ groups;

Q is selected from an optionally substituted $C_{1-2}$ alkylene, wherein said optional substituents are one to three $R^{10}$ groups;

$R^{10}$ is selected from alkyl, aryl, heteroaryl, cycloalkyl, spirocycloalkyl, heterocycloalkyl, arylalkoxy, F, Cl, Br, I, $CF_3$, $NR^{31A}R^{31B}$, $OR^{30}$, $OCF_3$, O—$Si(R^{29})_3$, O-tetrahydropyranyl, ethylene oxide, $(CH_2)_pOR^{30}$, $OR^{28}$, and a monosaccharide wherein each hydroxyl group of the monosaccharide is independently either unsubstituted or is replaced by H, alkyl, or alkoxy;

$R^{11}$ is selected from H and optionally substituted alkyl, wherein said optional substituents are one to three $R^{10}$ groups;

$R^{13}$ is independently selected from optionally substituted cycloalkyl, and optionally substituted heterocycloalkyl, wherein said optional substituents are one to three $R^{10}$ groups;

$R^{18}$ and $R^{19}$ are each independently selected from H, optionally substituted alkyl, optionally substituted aryl, optionally substituted heteroaryl, optionally substituted cycloalkyl, and optionally substituted heterocycloalkyl, wherein said optional substituents are one to three $R^{10}$ groups;

$R^{20}$ is selected from H, optionally substituted alkyl, optionally substituted alkenyl, optionally substituted alkynyl, optionally substituted aryl, optionally substituted arylalkyl, optionally substituted heteroaryl, optionally substituted cycloalkyl, and optionally substituted heterocycloalkyl, wherein said optional substituents are one to three $R^{10}$ groups;

$R^{22}$ is optionally substituted $C_5$-$C_{10}$ alkyl, wherein said optional substituents are one to three $R^{10}$ groups;

$R^{27}$ is selected from optionally substituted cycloalkyl, wherein said optional substituents are one to three $R^{10}$ groups;

$R^{28}$ is the residue of an amino acid after the removal of the hydroxyl moiety from the carboxyl group thereof;

$R^{29}$ is H or alkyl;

$R^{30}$ is H, alkyl, aryl, arylalkyl, heteroaryl, cycloalkyl, or heterocycloalkyl;

$R^{31A}$ and $R^{31B}$ are each independently selected from H, alkyl, and arylalkyl, or together with the nitrogen to which they are attached form a heterocycloalkyl;

$R^{32}$ is optionally substituted aryl, wherein said optional substituents are one to three $R^{10}$ groups;

$R^{33}$ is selected from optionally substituted cycloalkyl, optionally substituted heteroaryl, and optionally substituted heterocycloalkyl, wherein said optional substituents are one to three $R^{10}$ groups;

p is independently selected from 1, 2, 3, and 4;

x is 0 or 1;

or a stereoisomer or salt form thereof, said method comprising the steps of:

i) contacting said compound of formula (I) with a metal hydride together with an activating agent selected from a mineral, organic or Lewis acid in a solvent; and optionally ii) recovering the obtained compound of formula (II) or a stereoisomer or salt form-thereof.

2. The method of claim 1, wherein the metal hydride is selected from an aluminium hydride, or a borohydride.

3. The method of claim 1, wherein the activating agent is a Lewis acid.

4. The method of claim 1, wherein ring B is a 5-membered aromatic ring in which one or two carbon atoms are replaced with a nitrogen atom.

5. The method of claim 1, wherein $R^1$ is H.

6. The method of claim 1, wherein $R^2$ is H.

7. The method of claim 1, wherein the B ring is

8. The method of claim 1, wherein the compound of formula (II), or a stereoisomer or salt form thereof, has the general formula (IIc):

(IIc)

9. The method of claim 8, wherein the compound of formula (II) is
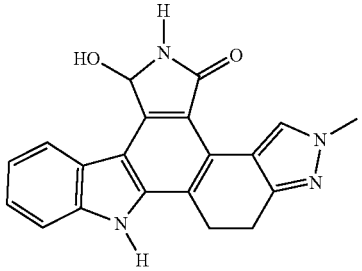
(IId)
or a stereoisomer or salt form thereof.
10. The method of claim 9 wherein the metal hydride is selected from an aluminium hydride, or a borohydride.
11. The method of claim 9 wherein the activating agent is a Lewis acid.
12. The method of claim 11 wherein the Lewis acid is selected from $MgCl_2$, $CaCl_2$, $CeCl_3$, or $TiCl_4$.
* * * * *